United States Patent [19]

Mori

[11] Patent Number: 4,936,663
[45] Date of Patent: Jun. 26, 1990

[54] LIGHT RADIATOR

[76] Inventor: Kei Mori, 3-16-3-501, Kaminoge, Setagaya-ku, Tokyo, Japan

[21] Appl. No.: 371,345

[22] Filed: Jun. 26, 1989

[30] Foreign Application Priority Data

Aug. 10, 1988 [JP] Japan .................................. 63-200414

[51] Int. Cl.⁵ .............................................. G02B 6/00
[52] U.S. Cl. .............................. 350/96.15; 350/96.10; 362/32
[58] Field of Search ............... 350/96.15, 96.20, 96.10, 350/96.29; 362/32

[56] References Cited

U.S. PATENT DOCUMENTS

| 4,669,817 | 6/1987 | Mori | 350/96.20 X |
| 4,678,279 | 7/1987 | Mori | 350/96.10 X |
| 4,730,890 | 3/1988 | Kashimura et al. | 350/96.20 |
| 4,812,008 | 3/1989 | Tokumaru et al. | 350/96.20 X |

Primary Examiner—John D. Lee
Assistant Examiner—Phan T. Heartney
Attorney, Agent, or Firm—Jordan and Hamburg

[57] ABSTRACT

A light radiator comprises a light-guide rod and a transparent tube. The light-guide rod has a slotted portion or a concave portion on its' body's circumference. The transparent tube is closely fitted to the light-guide rod to seal watertight the slotted portion or the concave portion of the rod. The transparent tube is made of thermally shrinkable material.

4 Claims, 4 Drawing Sheets

United States Patent [19]

Mori

[11] Patent Number: 4,936,663
[45] Date of Patent: Jun. 26, 1990

[54] LIGHT RADIATOR

[76] Inventor: Kei Mori, 3-16-3-501, Kaminoge, Setagaya-ku, Tokyo, Japan

[21] Appl. No.: 371,345

[22] Filed: Jun. 26, 1989

[30] Foreign Application Priority Data

Aug. 10, 1988 [JP] Japan .................. 63-200414

[51] Int. Cl.⁵ .................................. G02B 6/00
[52] U.S. Cl. ......................... 350/96.15; 350/96.10; 362/32
[58] Field of Search ............. 350/96.15, 96.20, 96.10, 350/96.29; 362/32

[56] References Cited

U.S. PATENT DOCUMENTS

| | | | |
|---|---|---|---|
| 4,669,817 | 6/1987 | Mori | 350/96.20 X |
| 4,678,279 | 7/1987 | Mori | 350/96.10 X |
| 4,730,890 | 3/1988 | Kashimura et al. | 350/96.20 |
| 4,812,008 | 3/1989 | Tokumaru et al. | 350/96.20 X |

*Primary Examiner*—John D. Lee
*Assistant Examiner*—Phan T. Heartney
*Attorney, Agent, or Firm*—Jordan and Hamburg

[57] ABSTRACT

A light radiator comprises a light-guide rod and a transparent tube. The light-guide rod has a slotted portion or a concave portion on its' body's circumference. The transparent tube is closely fitted to the light-guide rod to seal watertight the slotted portion or the concave portion of the rod. The transparent tube is made of thermally shrinkable material.

4 Claims, 4 Drawing Sheets

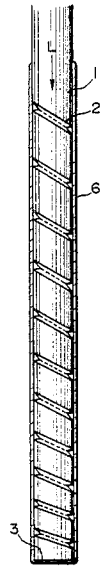

FIG. 3  FIG. 4  FIG. 5
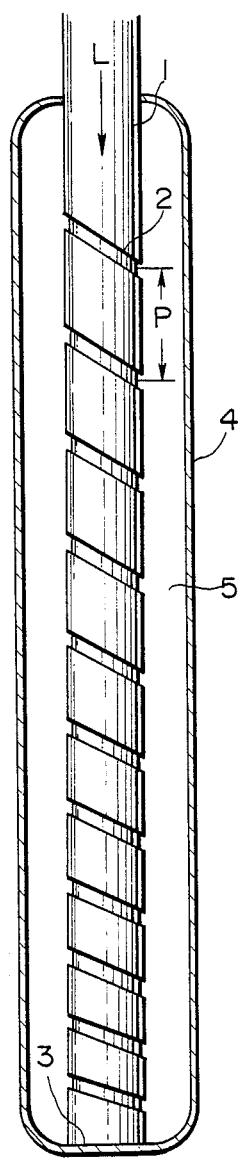
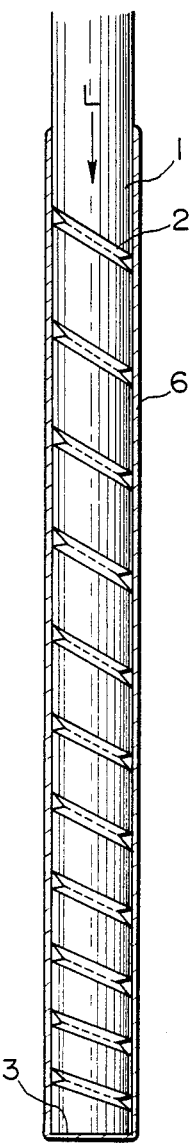
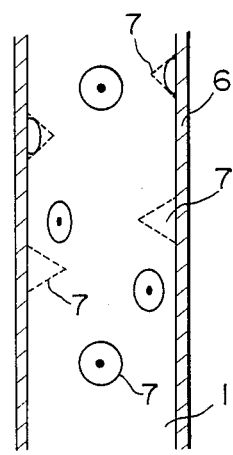
FIG. 6
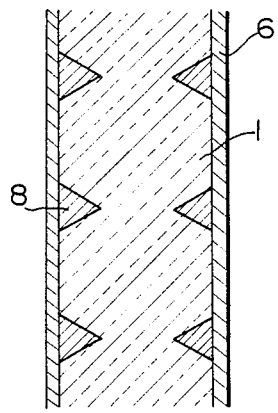

LIGHT RADIATOR

BACKGROUND OF THE INVENTION

The present invention relates to a light radiator capable of effectively and diffusedly radiating into water or other dirty places the light transmitted through a fiber optic cable or the like, in particular, a light radiator to be preferably used as a source of light energy for the photosynthetic process used in producing chlorella and other like organic substances.

In recent years, in relation to the necessity for saving energy, the effective utilization of solar energy has been actively studied and developed in various fields. The most effective utilization of solar energy is as light energy without its further being converted into thermal or electrical energy. With this in mind, the present applicant has proposed various methods and systems for channeling solar rays focused by means of a lens system, or the like, into a fiber optic cable and to transmit the same therethrough to wherever the light is needed for illumination or other purposes, as for example, for promoting the cultivation of plants, for the propagation of chlorella, for feeding fishes, for giving beauty treatments through sunbathing, for giving medical treatments through light radiation etc. If light rays are emitted from the cut end of a fiber optic cable, they can be radiated only within a small radiation angle of about 46° since focused light rays have a certain directivity. Therefore, the desired light radiation for the above-mentioned purposes may not be obtained if light is directly emitted from the cut end of the fiber optic cable. In order to solve this problem, the present applicant has also proposed various kinds of light radiators which can effectively diffuse the light rays transmitted through a fiber optic cable and to radiate the same to any desired place.

On fish farms, feeding small fish requires a great amount of zoo-plankton which eats chlorella to propagate itself. To effectively propagate chlorella it is necessary to properly supply the chlorella with sunlight and carbon dioxide. Generally, when chlorella increases, the light is obstructed and cannot reach the chlorella that is in the deeper areas, that is, the light which is obstructed cannot be distributed evenly to all of the chlorella plants. In view of this problem, in the past, the present applicant has proposed various chlorella cultivating apparatus which are capable of equally providing light energy to all of the chlorella in a cultivating tank by using a large number of 'pointed' light ray sources properly arranged therein.

A light radiator previously proposed by the present applicant comprises a light guide and a groove spirally cut on the surface of said light guide.

The light, introduced into the light guide, is reflected on a grooved portion thereof and effectively radiated therefrom for use as illumination and for other intended purposes as mentioned above.

In this case a substantially uniform radiation of the light from the whole body of the light guide may be realized if the spiral groove is made in such a way that the spiral pitch gradually becomes narrow or the groove itself gradually deepens in the direction of the light. Furthermore, when a reflecting plate or the like is placed at the end-face of the light guide, the light reflected by the reflecting plate enters into the light guide and then is radiated therefrom.

The light guide may be hermetically enclosed in a semi-transparent or transparent container to protect the light guide from being damaged by striking and also to eliminate the possibility of injury to a person's hand by the edge of its slotted or concave portion. Furthermore, when the light guide, thus protected in a container, is used in water as a light source for cultivating chlorella, or for feeding fishes it can be protected from a kind of fur forming on its surface.

Since the light guide is surrounded by an air layer in the container, the light can be radiated therethrough at a desirable angle and/or can be scattered as needed.

If the light guide, without the protective container, is used in water, its slotted or concave portion is filled with water, resulting in the light being radiated only from the limited end-surface of the light guide since the light reflection coefficiency scarcely changes at the slotted or concave portion.

In the above-mentioned light radiator there is a gap between the light guide and the container. In the case of placing a large number of said light radiators in a tank filled with a solution for cultivating chlorella, the density of the light guides can be reduced in relation to the total of the above-mentioned gaps.

SUMMARY OF THE INVENTION

It is an object of this invention to provide a light radiator suitable for use as a light source for cultivating chlorella and water organisms and for promoting the photosynthetic process itself.

It is another object of the present invention to provide a light radiator having a diameter nearly like that of a light-guide rod.

BRIEF DESCRIPTION OF THE DRAWINGS

FIG. 2 is a view for explaining a practical example for introducing light rays into a fiber optic cable;

FIG. 3 is a view for explaining an embodiment of a light radiator previously proposed by the present applicant;

FIGS. 4 to 6 illustrate respectively light radiators embodying the present invention;

DESCRIPTION OF THE PREFERRED EMBODIMENTS

Figure 1:
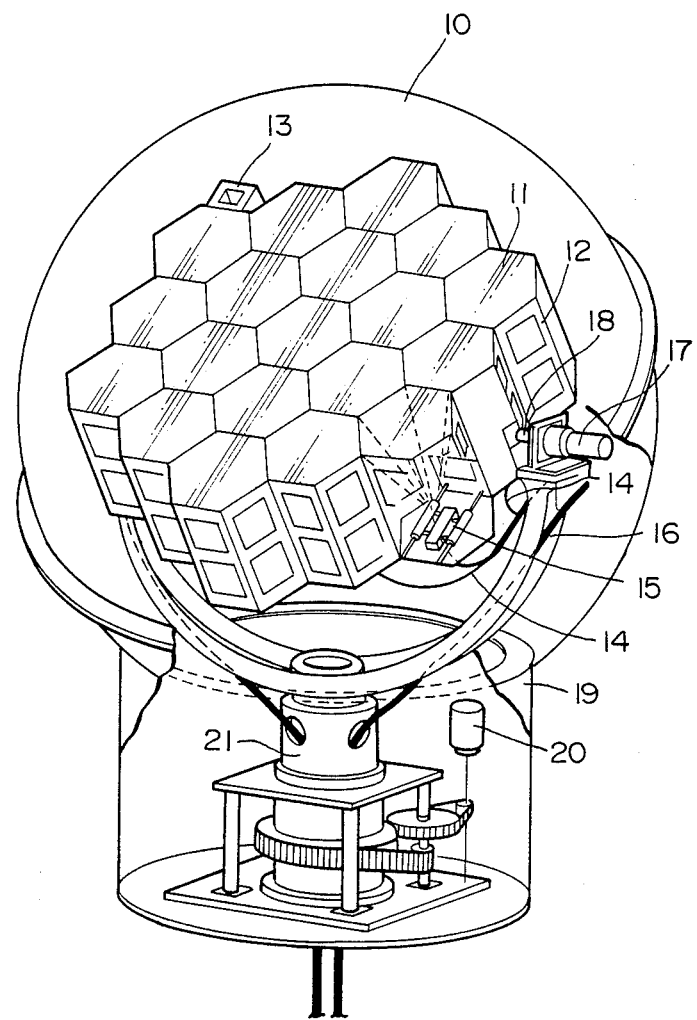
FIG. 1 is a view illustrating a solar ray collecting device which serves as an example for a system for introducing light rays into a fiber optic cable.

FIG. 1 is a construction view for illustrating, by way of example, a solar ray collecting device for guiding the sunlight into the aforesaid fiber optic cable. In FIG. 1, numeral 10 is a transparent capsule, 11 is a Fresnel lens, 12 is a lens holder, 13 is a solar-positioning sensor, 14 is an optical fiber or a fiber optic cable consisting of a large number of optical fibers having light-receiving end-surfaces set on the focal plane of the Fresnel lens system, 15 is a holder of the fiber optic cable, 16 is an arm, 17 is a pulse motor, 18 is a horizontal rotary shaft to be driven by the pulse motor 17, 19 is a base for supporting the protective capsule 10, 20 is a pulse motor and 21 is a vertical rotary shaft to be driven by the pulse motor 20.

The direction of the sun is detected by means of the solar position sensor 13 and its detection signal controls the pulse motors 17 and 18 of the horizontal and vertical rotation shafts 18 and 19 respectively so as to always direct the solar positioning sensor toward the sun, and the sunlight focused by the lens 11 is guided into the fiber optic cable 14 through its end-surface set at the focal point of the lens. All of the light guides 14, separately placed at each lens, are bundled together into a fiber optic cable bundle, the free end of which is led to any place where light radiation is needed for the aforementioned purposes.

FIG. 2 is a view for explaining how to guide the solar rays collected by the above-mentioned lens 11 into the fiber optic cable. In FIG. 2, 11 is a Fresnel lens and 14 is a light guide which receives the sunlight focused by the lens 11 and which transmits the same to any desired place. In case of focusing the sunlight through the lens system, the solar image has a central portion consisting of almost white light and a circumferential portion containing therein a large amount of the light components having wave-lengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3. Consequently, as shown in FIG. 2, when the light-receiving end-surfaces of the light guides are set at position P1, it is possible to collect sunlight which contains many blue color components at the circumferential portion thereof. When the light-receiving end-surfaces of the light guides are set at position P2, it is possible to collect sunlight containing many green color components at the circumferential portion thereof. When the light-receiving end-surfaces of the fiber optic cable are set at position P3 it is possible to collect sunlight containing many red color components at the circumferential portion thereof. In each case, the diameter of the light guide 14 can be selected in accordance with the light components to be collected. For instance, the required diameters of the fiber optic cables are D1, D2 and D3, respectively, depending on the colors of the light rays to be stressed, i.e. the blue, green and red colors. In such a way, the required amount of light guides can be saved and thereby the sunlight containing therein plenty of the desired color components can be collected most effectively.

And further, as shown in FIG. 2, if the diameter of the light-receiving end-surface of the light guide is enlarged to D0, it may be possible to collect visible light containing therein all of its wavelength components. The fiber optic cable 14 may be pre-set at the focal point of the lens system in the manufacturing process or they may be left in an adjustable condition in the axial direction of the lens system to allow the user to adjust and fix said light guides depending upon the desired color of the light to be obtained. By selecting the wave-length of the light components to be introduced into the fiber optic cable, it becomes possible to use the light radiating system more effectively for various purposes.

FIG. 3 is an enlarged sectional side view for explaining a light radiator previously proposed by the present applicant. In FIG. 3, 1 is a light guide and 2 is a groove spirally cut on the surface of the light guide's body.

The solar rays or artificial light rays focussed by using lenses and guided into a fiber optic cable as mentioned above are transmitted therethrough and introduced into the light guide 1.

The light L, introduced into the light guide 1, is reflected on a grooved portion thereof and effectively radiated therefrom for use in illumination and for other intended purposes.

In this case a substantially uniform radiation of the light L from the whole body of the light guide may be realized if the spiral groove 2 is made in such a way that the spiral pitch P gradually becomes narrow or the groove itself gradually deepens in the direction of the light L. Furthermore, when a reflecting plate 3, or the like, is placed at the end-face of the light guide, the light reflected by the reflecting plate enters into the light guide 1 and then it is radiated therefrom.

As shown in FIG. 3, the light guide may be used hermetically enclosed in a semi-transparent or transparent container 4 to protect the light guide from being damaged by striking and also to eliminate the possibility of injury to a person's hand by the edge of its slotted or concave portion. Furthermore, when the light guide, thus protected in a container, is used in water as a light source for cultivating chlorella, it can be protected from a kind of fur forming on its surface.

Since the light guide is surrounded by an air layer 5 in the container, the light can be radiated therethrough at a desired angle and/or can be scattered as needed.

If the light guide, without the protective container, is used in water, its slotted or concave portion 2 is filled with water, resulting in the light being radiated only from the limited end-surface of the light guide since the light reflection coefficiency scarcely changes at the slotted or concave portion 2.

In the above-mentioned light radiator there is a gap 5 between the light guide 1 and the container 4. In the case of placing a large number of said light radiators in a tank with a solution for cultivating chlorella, the density of the light guides can be reduced in relation to the total of the above-mentioned gaps.

In view of the foregoing, light radiator suitable for use in water, for example, as a light source for cultivating chlorella is desired for a long time.

FIG. 4 shows a light radiator embodying the present invention. In FIG. 4, numeral 4 designates a light-guide rod having a slotted or concave portion 2 thereon. In the same way as mentioned in the prior art, the light L, introduced into the light-guide rod 1 is reflected at the slotted or concave portion 2 and radiated therefrom.

According to the present invention, a light guide rod is tightly fitted into a transparent tube 6 so as to eliminate the possibility of filing the slotted or concave portion of the light-guide rod and therefore to realize the effective radiation of the light through the transparent tube 6. If this transparent tube is the thermal shrinking type, it is easily fitted onto the surface of the light guide rod.

The construction and shape of the slotted or concave portion are not limited to those shown in FIG. 4.

The stated portion of the light guide rod may be made in the shape of a ring or of discontinuous concave shapes at any desired place on the rod's body as shown in FIG. 5. In the above-mentioned embodiment, the whole surface of the light guide rod 1 is covered in the transparent tube 6. It is also possible to bind or fit a reflecting element 8 to each slotted or concave portion as shown in FIG. 6. When the outlet end of the light-guide rod is provided with a reflecting mirror 3, as mentioned above in the prior art's embodiment, the whole of the light introduced into the light guide rod 1 can be effectively radiated in the direction of the rod 1.

Figure 7:
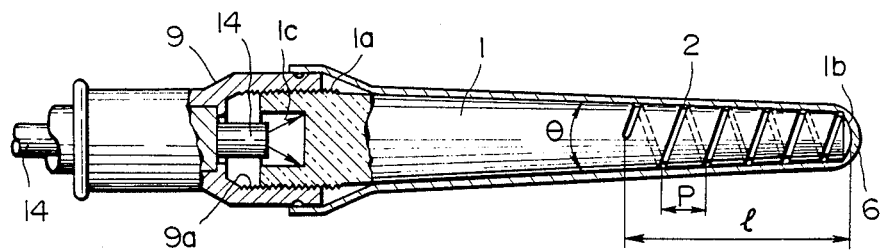
FIGS. 7 and 8 are construction views for explaining respective light radiators embodying the present invention.
Figure 8:
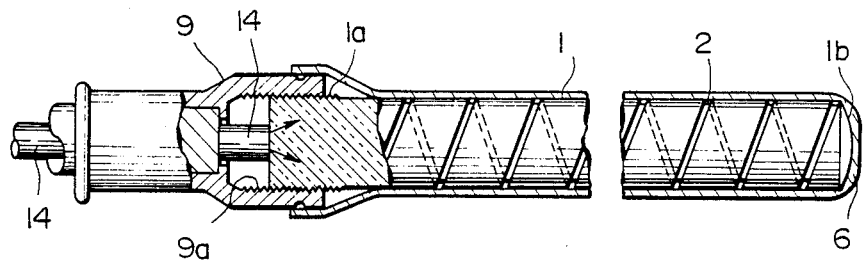

FIGS. 7 and 8 are construction views for explaining the respective light radiation devices embodying the present invention. In FIGS. 7 and 8, numeral 14 is a fiber optic cable as mentioned in FIG. 1, 9 is a connector attached to the light-emitting end of said fiber optic cable 14, 1 is a light radiator comprising a light-guide rod made of acrylic resin or the like and 6 is a thermal-shrinking type transparent tube. As shown in FIG. 7, the connector 9 has an inner thread 9a at least at its open-ended portion and the radiator 1 has an outer thread 1a at its one end by which said radiator is connected to said connector's thread 9a. The radiator can be used when its threaded portion 1a engages the connector's threaded portion 9a.

In the embodiment shown in FIG. 7, the light radiator, comprising a tapered light-guide rod 1 which has a thread 1a at the circumference of one end of a large diameter and a spiral groove 2 at its tapered portion. The spiral groove 2 can be selected for its length and pitch. Accordingly, any desired light distribution characteristics may be obtained by selecting a tapered angle $\theta$, a spiral pitch P and the proper length of the spiral groove. Specifically, if the tapered light-guide rod 1 has no spiral groove 2, light rays introduced into the rod are emitted mainly from the tip portion 1b of the rod. On the other hand, the light-guide rod has a spiral groove 2 allowing it to emit the light rays from a wide portion including the tip. For example, in the case when the light radiator is inserted into an opening of the human body such as the mouth, nose or anus to radiate light rays for giving medical treatments thereat, the light can be radiated not only forward from the tip portion but also sideways from the cylindrical surface of the end portion of its light-guide rod. Particularly, the radiator may be easily put into the anus to more effectively carry out the intended medical treatment.

FIG. 8 is a view for explaining an another embodiment of a light radiator according to the present invention. In FIG. 8, the light radiator comprises a cylindrical light-guide rod with a circumferential spiral groove 2 which is constructed in such a way that its depth becomes deeper or its spiral pitch becomes smaller as the groove gets nearer to the rod's tip 1b. Such a light radiator can radiate the light evenly from the grooved portion of its rod and therefore can be used as a linear light source.

As is apparent from the foregoing description, according to the present invention, it may be possible to provide a light-radiator having a diameter nearly like that of a light guide rod. In the case of cultivating chlorella it is possible to install a larger number of said light radiators so as to increase the production of chlorella.

I claim:

1. A light radiator for use as a source of light energy in a photosynthetic process used for cultivating chlorella and other organic substances, the combination comprising a solar ray collecting means for collecting solar rays and guiding said collected solar rays into a light guide rod adapted to be immersed in a liquid substance for cultivating chlorella and other organic substances, said light guide rod having groove means for reflecting said light rays such that said reflected light rays are radiated from said groove means of said light guide rod, and a thermal shrunk transparent tube on said light guide rod tightly contacting said light guide rod after having been applied to said light guide rod by thermal shrinking, said thermal shrunk transparent tube extending over said groove means without passing into said groove means so as to enable said groove means to effectively radiate said light rays therefrom.

2. A light radiator according to claim 1 wherein said light guide rod has a cylindrical configuration having an outer cylindrical surface, said groove means extending radially inwardly from said circumferential surface, said thermal shrunk transparent tube having an inner diameter, said tube having first portions overlying said groove means and second portions disposed between said groove means, the inner diameter of said tube at said first and second portions being equal.

3. A light radiator according to claim 2 wherein said groove means and sections of said tube overlying said groove means define hermetically sealed groove enclosures.

4. A light radiator according to claim 3 wherein said groove enclosures have air sealed therein.

* * * * *